US011007333B2

(12) United States Patent
Kimm et al.

(10) Patent No.: US 11,007,333 B2
(45) Date of Patent: *May 18, 2021

(54) SYSTEM AND METHOD FOR SUPPORTING SUB-PHYSIOLOGIC AND PHYSIOLOGIC TIDAL VOLUMES IN SPONTANEOUS OR NON-SPONTANEOUS BREATHING DURING HIGH FREQUENCY VENTILATION

(71) Applicant: KONINKLIJKE PHILIPS N.V., Eindhoven (NL)

(72) Inventors: Gardner Kimm, Carlsbad, CA (US); Smita Garde, Irvine, CA (US); Mabini Arcilla, San Diego, CA (US)

(73) Assignee: Koninklijke Philips N.V., Eindhoven (NL)

( * ) Notice: Subject to any disclaimer, the term of this patent is extended or adjusted under 35 U.S.C. 154(b) by 381 days.

This patent is subject to a terminal disclaimer.

(21) Appl. No.: 16/050,275

(22) Filed: Jul. 31, 2018

(65) Prior Publication Data

US 2018/0333549 A1    Nov. 22, 2018

Related U.S. Application Data

(63) Continuation of application No. 13/515,458, filed as application No. PCT/IB2010/055537 on Dec. 1, 2010, now Pat. No. 10,058,664.

(Continued)

(51) Int. Cl.
*A61M 16/00* (2006.01)
*A61M 16/20* (2006.01)
*A61M 16/12* (2006.01)

(52) U.S. Cl.
CPC .... *A61M 16/0057* (2013.01); *A61M 16/0069* (2014.02); *A61M 16/0096* (2013.01);
(Continued)

(58) Field of Classification Search
CPC ............ A61M 16/0057; A61M 16/204; A61M 16/205; A61M 16/0096; A61M 16/20;
(Continued)

(56) References Cited

U.S. PATENT DOCUMENTS

| 4,495,947 A * | 1/1985 | Motycka ........... A61M 16/0057 |
| | | 128/204.21 |
| 165,398 A | 7/1987 | Wolf |

(Continued)

FOREIGN PATENT DOCUMENTS

| EP | 0140487 A1 | 8/1985 |
| EP | 1106197 A2 | 6/2001 |

(Continued)

OTHER PUBLICATIONS

Van Heerde et al: "Unloading Work of Breathing During High-Frequency Oscillatory Ventilation: A Bench Study", Critical Care 2006, vol. 10, No. 4, pp. 1-7.

*Primary Examiner* — Kendra D Carter
*Assistant Examiner* — Jonathan S Paciorek
(74) *Attorney, Agent, or Firm* — Daniel H. Brean (57) ABSTRACT

A method of providing high frequency ventilation to a patient, comprises delivering a flow of breathing gas to the patient, the flow of breathing gas having a first positive pressure level and a second positive pressure level, the first and second positive pressure levels alternating with one another in a plurality of cycles in the flow of breathing gas to have a frequency and an amplitude, the flow of breathing gas to the patient generating a mean airway pressure; determining whether the patient is breathing spontaneously or is trying to breath spontaneously; and, in response to the determination that the patient is breathing spontaneously or trying to breath spontaneously or according to the user settings for HFV and user intervention for non-spontaneous breathing patient, adjusting the mean airway pressure, (Continued)

modulating the frequency and duty cycle of the flow of breathing gas, or modulating the level of flow and pressure amplitude of the breathing gas, or two or more thereof.

19 Claims, 9 Drawing Sheets

Related U.S. Application Data (60) Provisional application No. 61/286,451, filed on Dec. 15, 2009.

(52) U.S. Cl.
CPC .......... *A61M 16/20* (2013.01); *A61M 16/204* (2014.02); *A61M 16/205* (2014.02); *A61M 16/0066* (2013.01); *A61M 16/024* (2017.08); *A61M 16/12* (2013.01); *A61M 2016/0021* (2013.01); *A61M 2016/0027* (2013.01); *A61M 2016/0036* (2013.01); *A61M 2016/0039* (2013.01); *A61M 2205/50* (2013.01); *A61M 2205/502* (2013.01); *A61M 2230/40* (2013.01); *A61M 2230/63* (2013.01); *A61M 2230/65* (2013.01)

(58) Field of Classification Search
CPC ............ A61M 16/0069; A61M 16/024; A61M 16/0066; A61M 16/12; A61M 2016/0021; A61M 2016/0027; A61M 2016/0036; A61M 2016/0039
See application file for complete search history.

(56) References Cited

U.S. PATENT DOCUMENTS

| | | |
|---|---|---|
| 4,719,910 A | 1/1988 | Jensen |
| 4,747,402 A | 5/1988 | Reese |
| 4,747,403 A | 5/1988 | Gluck |
| 4,773,411 A | 9/1988 | Downs |
| 4,788,974 A | 12/1988 | Phue |
| 4,805,612 A | 2/1989 | Jensen |
| 4,821,709 A | 4/1989 | Jensen |
| 4,838,259 A * | 6/1989 | Gluck ............... A61M 16/0096 128/204.21 |
| 5,092,326 A | 3/1992 | Winn |
| 5,107,830 A | 4/1992 | Younes |
| 5,165,398 A | 11/1992 | Bird |
| 5,419,768 A | 5/1995 | Kayser |
| 5,555,880 A | 9/1996 | Winter |
| 5,862,802 A | 1/1999 | Bird |
| 5,871,008 A | 2/1999 | Poon et al. |
| 5,931,160 A | 8/1999 | Gilmore |
| 6,390,092 B1 | 5/2002 | Leenhoven |
| 6,435,182 B1 | 8/2002 | Lutchen |
| 6,640,807 B2 | 11/2003 | Bennarsten |
| 7,000,610 B2 | 2/2006 | Bennarsten |
| 7,121,277 B2 | 10/2006 | Strom |
| 7,588,033 B2 | 9/2009 | Wondka |
| 7,770,580 B2 | 8/2010 | Kruger et al. |
| 2001/0007256 A1 | 7/2001 | Sugiura |
| 2005/0005936 A1 | 1/2005 | Wondka |
| 2007/0215154 A1 | 9/2007 | Borrello |
| 2008/0087284 A1* | 4/2008 | Krueger ............ A61M 16/0096 128/204.21 |

FOREIGN PATENT DOCUMENTS

| | | |
|---|---|---|
| JP | S6058165 A | 4/1985 |
| WO | 2003005886 A2 | 1/2003 |
| WO | 2005068005 A1 | 7/2005 |
| WO | 2008146264 A2 | 12/2008 |
| WO | 2009067554 A1 | 5/2009 |

* cited by examiner

SYSTEM AND METHOD FOR SUPPORTING SUB-PHYSIOLOGIC AND PHYSIOLOGIC TIDAL VOLUMES IN SPONTANEOUS OR NON-SPONTANEOUS BREATHING DURING HIGH FREQUENCY VENTILATION

This application is a continuation application of co-pending U.S. patent application Ser. No. 13/515,458 entitled "SYSTEM AND METHOD FOR SUPPORTING SUB-PHYSIOLOGIC AND PHYSIOLOGIC TIDAL VOLUMES IN SPONTANEOUS OR NON-SPONTANEOUS BREATHING DURING HIGH FREQUENCY VENTILATION" filed on Jun. 12, 2012, which in turn is the U.S. National Phase application under 35 U.S.C. § 371 of International Application No. PCT/IB2010/055537, filed on Dec. 1, 2010, which claims the benefit of U.S. Provisional Patent Application No. 61/286,451, filed on Dec. 15, 2009. These applications are hereby incorporated by reference herein.

FIELD OF THE INVENTION

The present invention relates to a positive airway pressure system for providing high frequency ventilation and, more particularly, to a positive pressure system and method of providing high frequency ventilation that facilitates sub-physiologic and physiologic tidal volumes during non-spontaneous breathing or spontaneous breathing efforts.

DESCRIPTION OF THE INVENTION

High frequency ventilation (HFV) is a ventilation strategy that uses sub-physiologic tidal volumes at supra-physiologic respiratory rates. This is used as lung protective ventilation strategy to reduce ventilator-induced lung injury (VILI) in adult, pediatric, and neonatal patients. This is achieved by delivering sub-physiologic (<dead-space) tidal volumes of from about 0.5 ml/kg to about 5 ml/kg at high frequency rates of from about 2 Hz to about 20 Hz. This mode of ventilation is more widely used for neonatal patients and is now regaining interest for adult patients with acute respiratory distress symptom (ARDS).

In HFV, gas exchange is achieved by using sub-deadspace tidal volumes, and this helps in recruiting and stabilizing lungs without lung injury. The gas exchange involves the mechanisms of bulk axial flow, inter-regional gas mixing, axial and radial dispersion, convective dispersion, and molecular diffusion, as compared to conventional ventilation where the mechanism is mainly bulk flow (convection) ventilation.

There are different types of HFV. In high frequency oscillatory ventilation (HFOV), the pressure oscillates above and below a set mean airway pressure. High frequency jet ventilation (HFJV) is another type of HFV where a brief duration high pressure of a jet of gas flow in a patient's airway is at a frequency of from about 10 Hz to about 20 Hz (from about 600 bpm to about 1200 bpm). High frequency flow interruption (HFFI) is yet another type of HFV where brief pulses of gas flow are delivered to a patient's airway at from about 5 Hz to about 15 Hz (from about 300 bpm to about 900 bpm) frequency. High frequency positive pressure ventilation (HFPPV) is typically known as the type of HFV where positive pressure pulses are used at higher frequency of breath rates of from about 2 Hz to about 25 Hz to deliver sub-physiologoc tidal volumes.

The use of HFV has been limited as a rescue mechanism for adult patients but is more commonly used for neonatal patients. Although HFV is primarily used to deliver sub-physiologic volumes, it also has the ability to deliver physiologic volumes that are needed in some cases, an example of which is to support spontaneous breathing in non-sedated patients.

SUMMARY OF THE INVENTION

In one embodiment of the invention, HFPPV control features are implemented to facilitate physiologic volumes in non-spontaneous breathing or spontaneous breathing efforts. More particularly, HFPPV mode facilitates or supports physiologic volumes during non-spontaneous breathing or spontaneous breathing efforts by controlling mean airway pressure with an active control of the exhalation valve. In another aspect of the invention, HFPPV mode facilitates physiologic volumes during non-spontaneous breathing or spontaneous breathing with active control of high frequency flow levels with breathing efforts. In a further aspect of the invention, HFPPV mode supports physiologic volumes during non-spontaneous breathing or spontaneous breathing efforts by changing the frequency and duty cycle of positive pressure ventilation.

In another embodiment of the invention, HFOV control features are implemented to facilitate physiologic volumes in non-spontaneous breathing or spontaneous breathing efforts. More particularly, HFOV mode facilitates or supports physiologic volumes during non-spontaneous breathing or spontaneous breathing efforts by controlling mean airway pressure with an active control of the exhalation valve. In another aspect of the invention, HFOV mode facilitates physiologic volumes during non-spontaneous breathing or spontaneous breathing with active control of high frequency flow levels with breathing efforts. In a further aspect of the invention, HFOV mode supports physiologic volumes during non-spontaneous breathing or spontaneous breathing efforts by changing the frequency and duty cycle of positive pressure ventilation.

In one embodiment of the invention, HFJV control features are implemented to facilitate physiologic volumes in non-spontaneous breathing or spontaneous breathing efforts. More particularly, HFJV mode facilitates or supports physiologic volumes during non-spontaneous breathing or spontaneous breathing efforts by controlling mean airway pressure. In another aspect of the invention, HFJV mode facilitates physiologic volumes during non-spontaneous breathing or spontaneous breathing with active control of high frequency flow levels with breathing efforts. In a further aspect of the invention, HFJV mode supports physiologic volumes during non-spontaneous breathing or spontaneous breathing efforts by changing the frequency and duty cycle of positive pressure ventilation.

The use of HFPPV ventilators in the manner described above facilitates physiologic volumes during non-spontaneous breathing or spontaneous breathing and maintains airway pressure with simultaneous control of mean airway pressure, of high frequency flow levels with breathing efforts, and of the frequency and duty cycle of positive pressure ventilation.

In another embodiment of the invention, the use of HFPPV ventilators in the manner described above delivers sub-physiologic volumes and maintains airway pressure with simultaneous control of mean airway pressure, of high frequency flow levels, and of the frequency and duty cycle of positive pressure ventilation.

In another embodiment of the invention, the use of HFOV ventilators in the manner described above delivers sub-physiologic volumes and maintains airway pressure with simultaneous control of mean airway pressure, of high frequency flow levels, and of the frequency and duty cycle of positive pressure ventilation.

In another embodiment of the invention, the use of HFJV ventilators in the manner described above delivers sub-physiologic volumes and maintains airway pressure with simultaneous control of mean airway pressure, high frequency flow levels, and the frequency and of duty cycle of positive pressure ventilation.

In another embodiment of the invention, one can obtain an estimate of physiologic volumes during non-spontaneous breathing or spontaneous breathing efforts from patient signals such as patient flow or patient pressure and/or from additional sensors and signals for robust detection.

In another embodiment of the invention, an algorithm adaptively sets the positive pressure ventilation (e.g., frequency, duty cycle, flow levels, or mean airway pressure) to deliver a set tidal volume in the course of HFV therapy.

In another embodiment of the invention, the HFPPV mode has been implemented as a newer mode of conventional ventilator with a extended range for frequency, duty cycle, flow levels, or mean airway pressure of positive pressure ventilation of from about 2 Hz to about 25 Hz.

In another embodiment of the invention, a method of providing positive pressure ventilation to a patient comprises delivering high frequency ventilation to the patient to support non-spontaneous breathing or spontaneous breathing efforts. The method further determines the need of physiologic volumes for the patient during non-spontaneous breathing as set by the user or for a patient exhibiting spontaneous breathing and, in response to that determination, controls the mean airway pressure with an active exhalation valve, modulates the frequency and the duty cycle of the ventilation, and modulates the amplitude of positive pressure pulses for high frequency ventilation.

In another embodiment of the invention, a pressure support system is provided that includes a pressure generating system, a patient circuit operatively coupled to the pressure generating system, and a controller operatively coupled to the pressure generating system. The controller is adapted to: (i) control the pressure generating system to deliver high frequency ventilation, (ii) determine the need of physiologic volumes for the patient during non-spontaneous breathing as set by the user or determine that the patient is breathing spontaneously, and (iii) in response to that determination, control the pressure generating system to proportionally vary or modulate the frequency, duty cycle, or amplitude of the ventilation or the mean airway pressure using an exhalation valve.

In another embodiment of the invention, a system and method provide physiologic volumes interspersed with high frequency sub-physiologic volumes by intermittently modulating the mean airway pressure.

In another embodiment of the invention, mean airway pressure is modulated by intermittently varying the exhalation resistance.

In another embodiment of the invention, mean airway pressure is modulated by intermittently varying the flow amplitude.

In another embodiment of the invention, mean airway pressure is modulated by intermittently varying the frequency.

In another embodiment of the invention, mean airway pressure is modulated by intermittently varying the duty cycle.

In another embodiment of the invention, mean airway pressure is modulated by intermittently varying any combination of exhalation resistance, flow amplitude, frequency, and duty cycle.

In another embodiment of a system of the invention, modulating mean airway pressure is meant to achieve physiologic volumes to provide for spontaneous breathing.

In another embodiment of a system of the invention, modulating mean airway pressure is meant to achieve physiologic volumes to provide for spontaneous breathing with pressure support.

In another embodiment of a system of the invention, modulating mean airway pressure is meant to provide for physiologic volumes in the absence of spontaneous breathing.

Therefore, it should now be apparent that the invention substantially achieves all the above aspects and advantages. Additional aspects and advantages of the invention will be set forth in the description that follows, and in part will be inherent from the description, or may be appreciated by practice of the invention. Moreover, the aspects and advantages of the invention may be realized and obtained by means of the instrumentalities and combinations particularly pointed out in the appended claims.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts.

DETAILED DESCRIPTION OF THE INVENTION

The present invention, in the various embodiments described herein, relates to a positive airway pressure ventilation system for providing high frequency ventilation that facilitates sub-physiologic and physiologic tidal volumes during non-spontaneous breathing or spontaneous breathing efforts. The present invention also contemplates that the therapy method as described herein in various embodiments is implemented in a microprocessor (or similar controller)-based positive airway pressure ventilation system that includes hardware to allow the microprocessor (or similar controller) to control the ventilation (i.e., the provision of breathing gas at specified pressures or frequencies) as described in greater detail herein.

Figure 1:
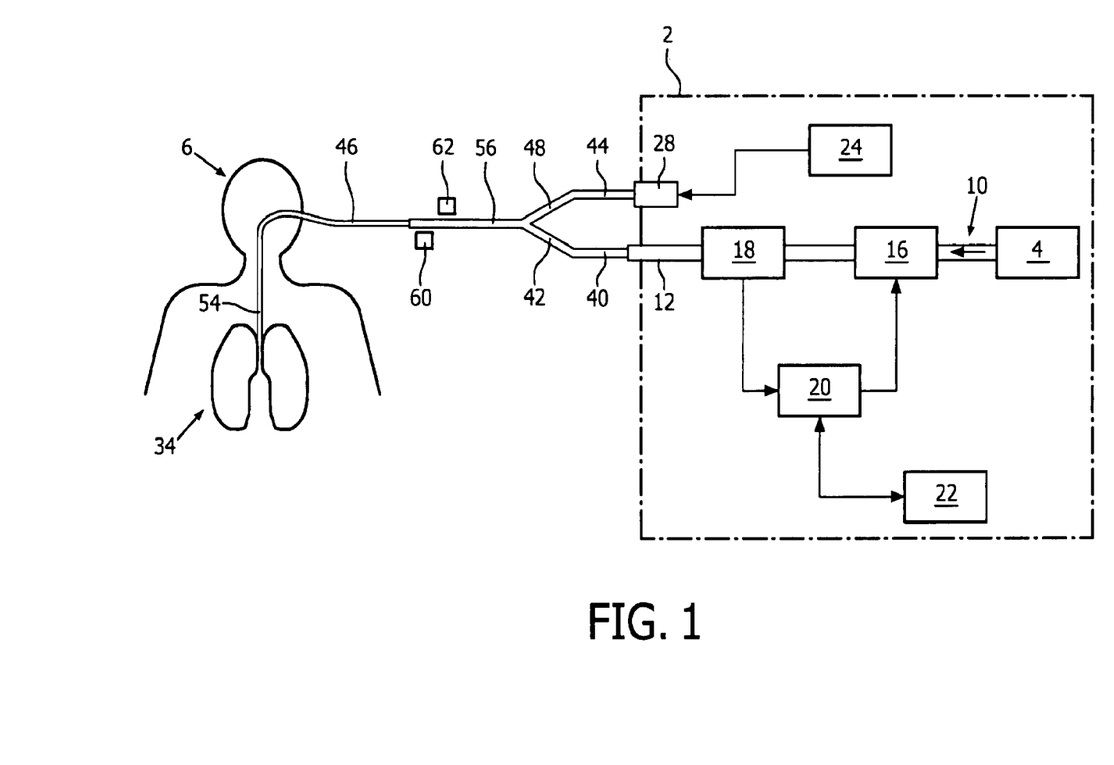
FIG. 1 is a schematic diagram of a pressure system for providing HFPPV according to one particular, non-limiting embodiment of the invention.

This invention can perhaps be better understood from the drawings, which are directed to a particular high frequency system, namely, HFPPV. FIG. 1 is a schematic diagram of a high frequency positive pressure ventilation system 2 for providing positive airway pressure ventilation to a patient. In FIG. 1, HFPPV system 2 comprises a gas flow generator 4, such as a blower, high pressure gas wall outlet, or a pressurized tank of gas that receives breathing gas or a combination of gases. Gas flow generator 4 generates a flow of breathing gas, such as air, oxygen, heliox, or other gases or a mixture thereof, for delivery to an airway of a patient 6. The pressurized flow of breathing gas, generally indicated by arrow 10 from gas flow generator 4, is delivered via a delivery conduit 12 to patient 6.

In the embodiment illustrated, HFPPV system 2 includes a flow controller in the form of a valve 16. Valve 16 controls the flow of breathing gas from the flow generator 4 delivered to patient 6. For present purposes, flow generator 4 and valve 16 are collectively referred to as a flow/pressure generating system because they act in concert to control the pressure and/or flow of gas delivered to the patient. However, it should be apparent that other techniques for controlling the flow rate and pressure of the gas that is delivered to the patient, such as varying the blower speed of flow generator 4, either alone or in combination with a pressure control valve, are contemplated by the present invention.

HFPPV system 2 further includes a flow sensor 18 that measures the flow of the breathing gas within delivery conduit 12. In the particular embodiment shown in FIG. 1, flow sensor 18 is interposed in line with delivery conduit 12. Flow sensor 18 generates a flow signal that is provided to a controller 20 and is used by controller 20 to determine the flow of gas to patient 6. Of course, other techniques for measuring the respiratory flow of patient 6 are contemplated by the present invention, such as, without limitation, measuring the flow directly at patient 6 or at other locations along delivery conduit 12, measuring patient flow based on the operation of flow generator 4, and measuring patient flow using a flow sensor upstream of valve 16. Controller 20 may be, for example, a microprocessor, a microcontroller or some other suitable processing device, that includes or is operatively coupled to a memory (not shown) that provides a storage medium for data and software executable by controller 20 for controlling the operation of HFPPV system 2, including controlling the flow of breathing gas to provide ventilation to patient 6 and to implement the HFV adjustments in the various embodiments described in detail elsewhere herein. Finally, an input/output device 22 is provided for setting various parameters used by HFPPV system 2, as well as for displaying and outputting information and data to a user, such as a clinician or caregiver.

HFV systems are well known and have been previously described in, e.g., U.S. Pat. No. 4,719,910, which is incorporated by reference as if set forth fully herein.

HFPPV system 2 includes a patient breathing circuit 40 that includes an intake or inspiration limb 42 and an expiration limb 44 with an active exhalation valve 28 that is controlled by an exhalation valve controller 24. Inspiration limb 42 connects to the airway of patient 6 through an intubator endotracheal or tracheal tube 46 via a Y-piece 48. Breathing circuit 40 may be made of standard flexible tubing that is used with ventilators or may be modified tubing suitable for delivery of HFPPV.

During operation, HFPPV system 2 delivers high frequency positive pressure pulses to the lungs 34 of patient 6 with a mean distending pressure called mean airway pressure (MAP). Typically, the mean airway pressure is adjustable within the range of from about 3 cm $H_2O$ to about 50 cm $H_2O$. The mean airway pressure is superimposed with oscillating pressure. The high frequency positive pressure delivery promotes gas exchange with lungs 34. Preferably, the frequency of HFPPV can be preprogrammed or manually adjusted on HFPPV system 2. Preferably, the pressure amplitude and the frequency of HFPPV can be set by an operator of HFPPV system 2 or the pressure amplitude and frequency can be set by an automated adaptive control algorithm in the controller. HFPPV system 2 also preferably comprises a user control (not shown) for mean airway pressure that can either increase or decrease the mean airway pressure delivered to patient 6.

Preferably, HFPPV system 2 includes an adjustable I:E ratio or an adjustable duty cycle, the range of which will vary based on the selected frequency of HFPPV.

HFPPV system 2 may have a display unit (not shown) that can display the user settings and monitored signals. Such a display unit could display additional information such as frequency, mean airway pressure, flow and pressure amplitude, gas mix levels, distal and proximal pressure readings, inspiration time, bias flow and the like. The display unit could be a computer monitor, LCD screen, or the like.

Endotracheal tube 46 of HFPPV system 2 has two ends—a distal end 54 that is positioned within the airway of patient 6 and a proximal end 56 that is located at Y-piece 48. A flow sensor 60 is preferably located in the proximal end 56 of endotracheal tube 46, and a pressure sensor 62 is preferably located in proximal end 56 of endotracheal tube 46. Pressure sensor 62 and flow sensor 60 are sufficiently sensitive such that they can measure the peak-to-peak pressure readings and patient flow respectively within endotracheal tube 46.

Figure 2:
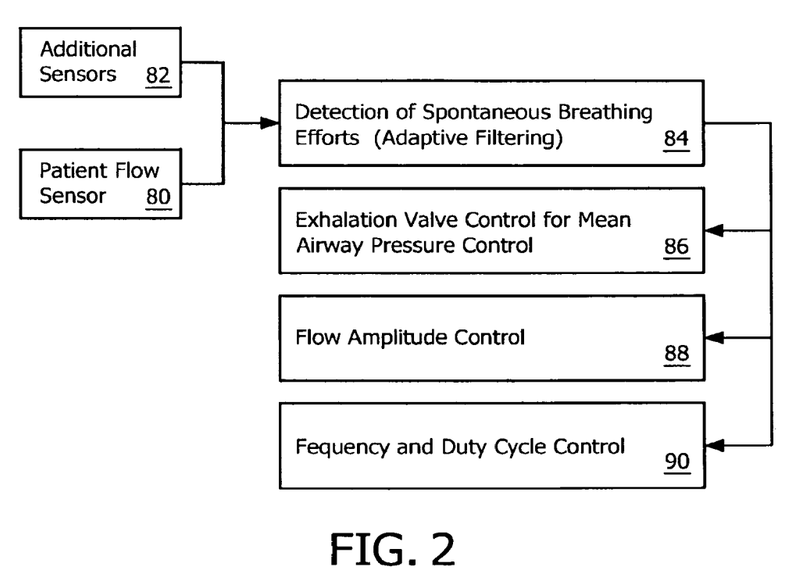
FIG. 2 is a schematic diagram of the HFPPV control of mean airway pressure according to the invention, with spontaneous breathing.

To facilitate sub-physiologic and physiologic tidal volumes for non-spontaneous breathing or spontaneous breathing efforts during HFPPV by controlling mean airway pressure (MAP) with an active exhalation valve, an active exhalation valve controls the mean airway pressure levels as shown in the schematic diagram of FIG. 2. Normally the HFPPV maintains the MAP at a fixed level during both inhalation and exhalation phases to provide adequate lung distension. The data from a patient flow sensor 80 and additional pressure and/or flow sensors and/or other sensors or user input 82 is processed in processor 84 to determine whether the patient is breathing spontaneously or is trying to breathe spontaneously or the user needs to deliver a physiologic volume to the patient. Signals from processor 84 are sent to control an exhalation valve 86 and/or to adjust the high frequency flow (pressure) control 88 or the frequency control 90 regarding the airway pressure ventilation to the patient.

Figure 3A:
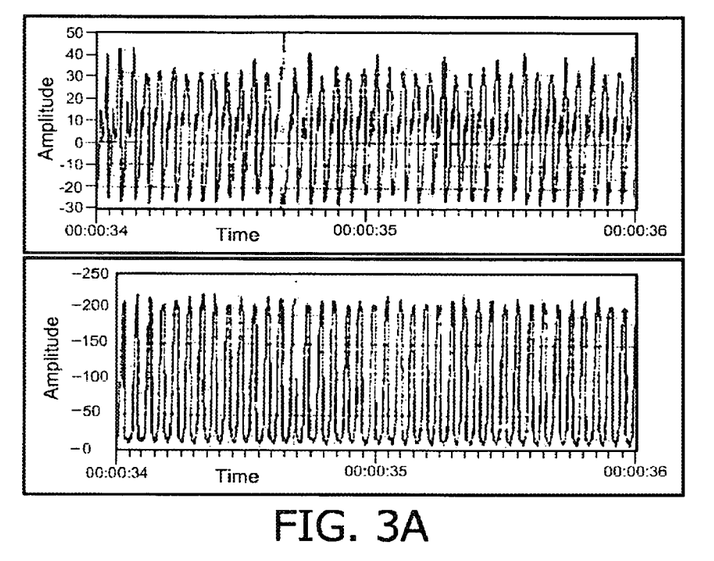
FIGS. 3A and 3B represent HFPPV pressure and flow patterns at two different frequencies.
Figure 3B:
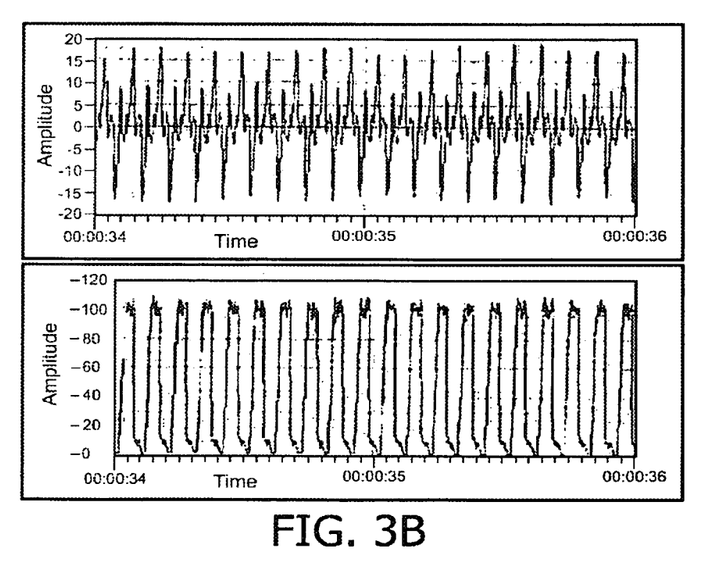

According to the invention, active control of an exhalation valve sets the level of MAP at the desired frequency and flow levels. In FIG. 3A the graph in the upper monitor represents the patient pressure over time at 25 Hz, whereas the graph in the lower monitor represents the patient flow rate over time at 25 Hz. The graphs in FIG. 3B represent the patient pressure and flow rate over time, respectively, at 10 Hz. This data represents HFPPV with fixed control of the exhalation valve.

Figure 4A:
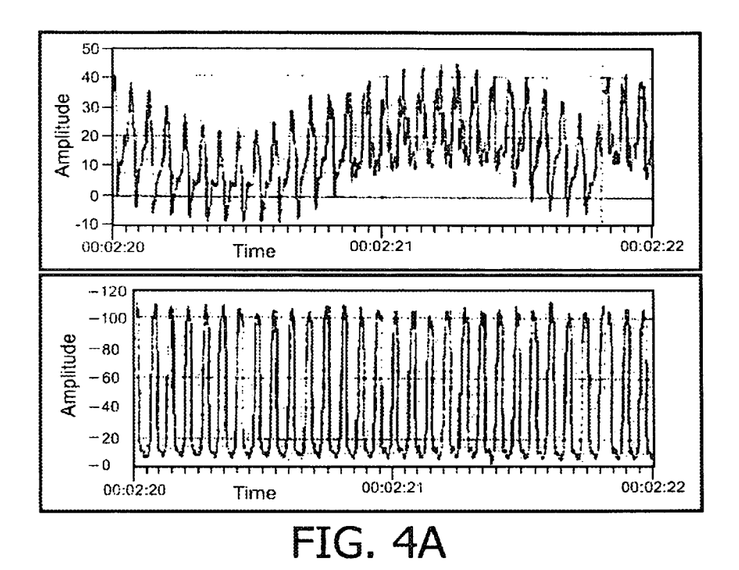
FIGS. 4A and 4B represent HFPPV pressure and flow patterns with MAP control implemented to support sinusoidal and bi-level control for inspiration and expiration phases of a breathing pattern, respectively.
Figure 4B:
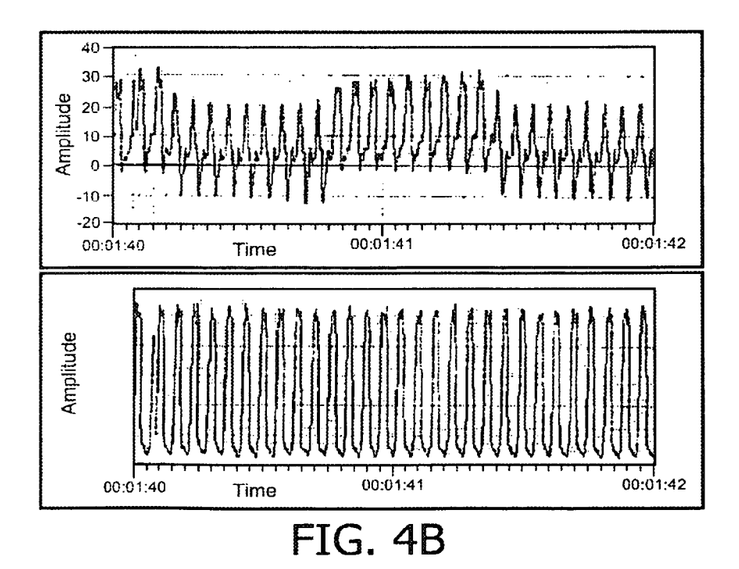

Active control of the exhalation valve with spontaneous breathing efforts during inhalation and exhalation phase is represented in FIGS. 4A and 4B. In FIG. 4A the graphs in the upper monitor represent the patient pressure over time with a sinusoidal breathing pattern, whereas the lower monitor represents the flow rate over time with that breathing pattern. The graphs in FIG. 4B represent the patient pressure and flow rate over time, respectively, with a bi-level control for an inspiration and expiration phases breathing pattern.

Figure 5A:
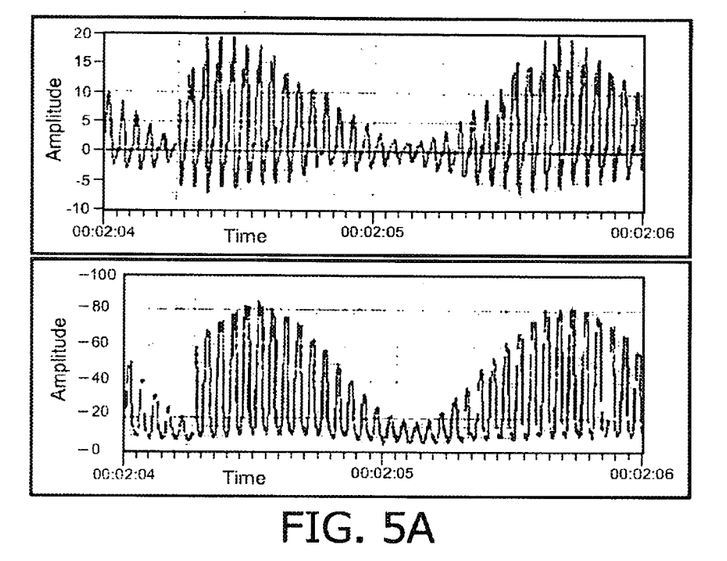
FIGS. 5A and 5B represent HFPPV pressure and flow patterns with active control of high frequency flow levels to support sinusoidal breathing pattern and bi-level control for inspiration and expiration phases of a breathing pattern, respectively.
Figure 5B:
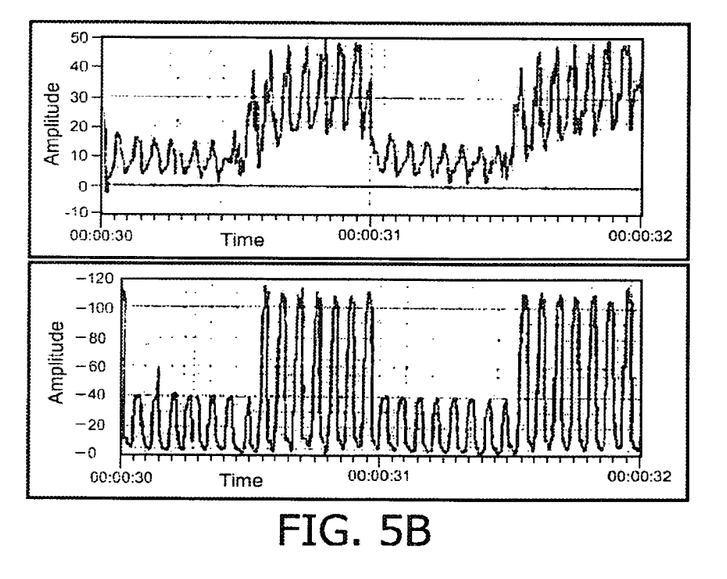

In one embodiment of the invention, providing sub-physiologic and physiologic tidal volumes during non-spontaneous breathing or spontaneous breathing is facilitated with active control of high frequency flow levels with breathing efforts. There is active control of high frequency flow levels for HFPPV that is controlled according to the user input or spontaneous breathing efforts, or control can be set to achieve bi-level control as shown in FIGS. 5A and 5B. In FIG. 5A, the graph in the upper monitor represents patient pressure over time in HFPPV with flow control and a sinusoidal breathing pattern, whereas the graph in the lower monitor represents flow rate over time under the same conditions. The graphs in FIG. 5B represent the patient pressure and flow rate over time, respectively, for bi-level control where the two flow levels correspond to the inhalation and exhalation phase of breathing cycle.

Figure 6A:
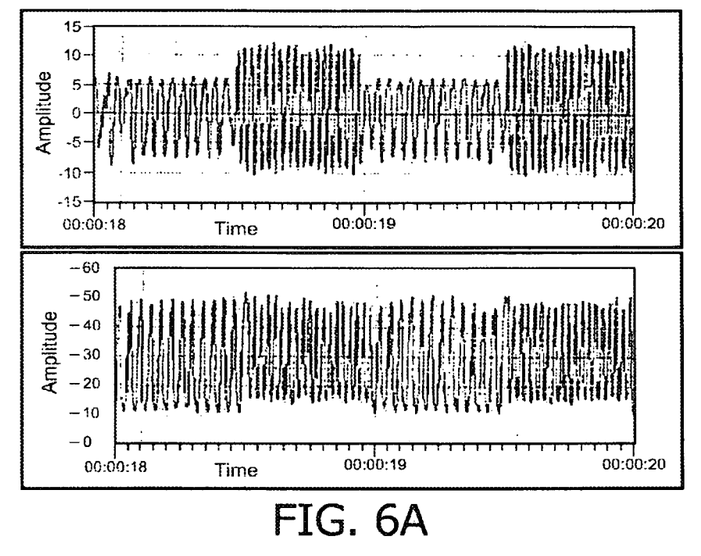
FIGS. 6A and 6B represent HFPPV pressure and flow patterns with active modulation of frequency of ventilation to support sinusoidal breathing pattern and a bi-level control for inspiration and expiration phases of a breathing pattern, respectively.
Figure 6B:
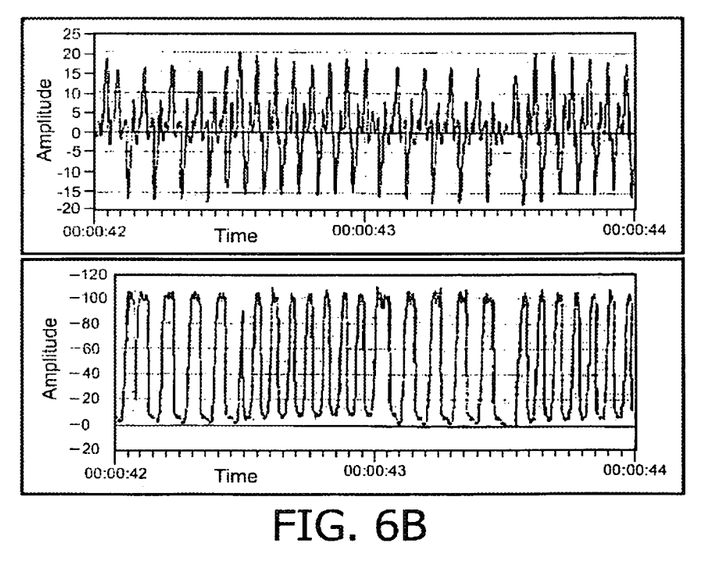

One embodiment of the invention includes the feature to control the frequency of HFPPV to improve gas exchange and support sub-physiologic and physiologic tidal volumes during non-spontaneous breathing or spontaneous breathing. Active control of the oscillation frequency can be controlled by user's input or proportionally according to the spontaneous breathing or it can be controlled in a bilevel manner, as set forth in FIGS. 6A and 6B. In FIG. 6A, the graph in the upper monitor represents patient pressure over time in HFPPV with flow control and a sinusoidal breathing pattern, whereas the graph in the lower monitor represents flow rate over time under the same conditions. The graphs in FIG. 6B represent the patient pressure and flow rate over time, respectively, for bi-level control.

Figure 7A:
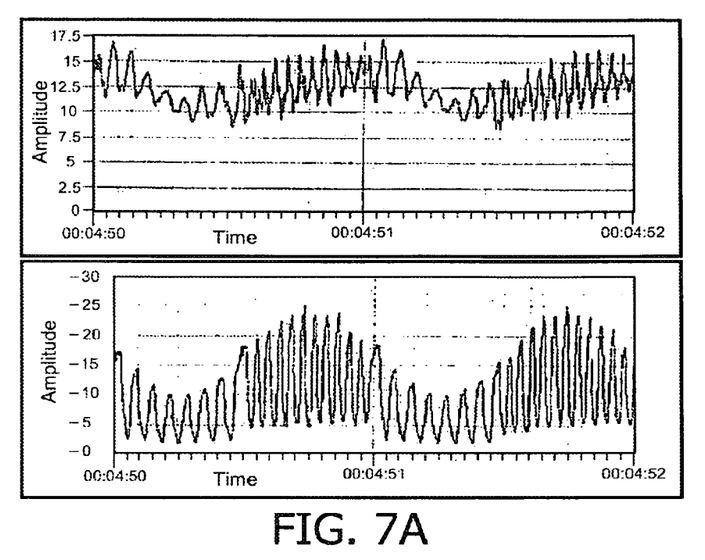
FIGS. 7A and 7B represent HFPPV pressure and flow patterns with simultaneous control of exhalation valve, flow level, and frequency of positive pressure ventilation with sinusoidal breathing pattern and bi-level control.
Figure 7B:
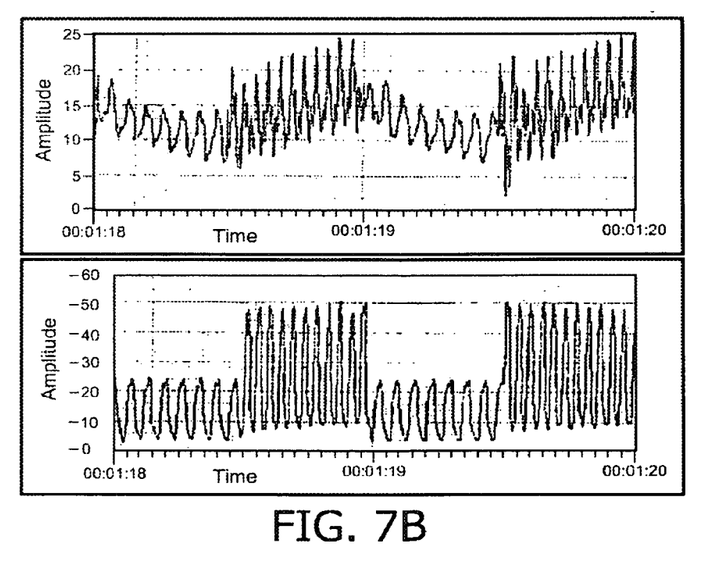

The invention also includes a feature for active control of mean airway pressure with simultaneous control of exhalation valve, high frequency flow levels and frequency. This feature allows additional HFPPV control mode to continuously and proportionally facilitate sub-physiologic and physiologic tidal volumes during non-spontaneous breathing or spontaneous breathing. In FIG. 7A, the graph in the upper monitor represents patient pressure over time in HFPPV with simultaneous control of the exhalation valve, flow level and oscillation frequency and a sinusoidal breathing pattern, whereas the graph in the lower monitor represents flow rate over time under the same conditions. The graphs in FIG. 7B represent the patient pressure and flow rate over time, respectively, for bi-level control during inspiration and expiration phases of spontaneous breathing pattern.

Figure 8:
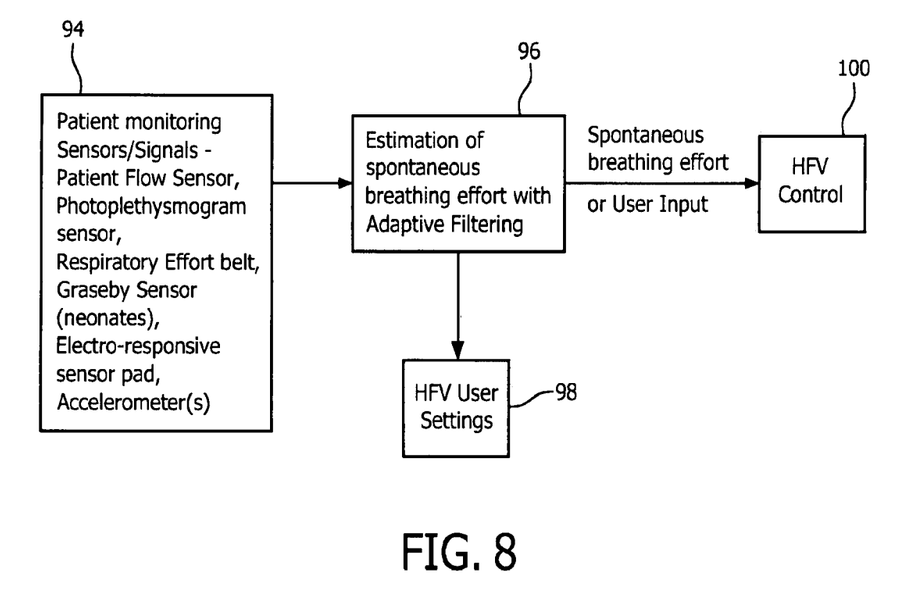
FIG. 8 is a schematic representation of an algorithm to adaptively set the high frequency positive pressure ventilation.

Spontaneous breathing is detected and/or predicted from high frequency patient flow signal and/or from additional sensors and signals for robust detection. The active control of HFPPV as described above is based on the level of spontaneous breathing efforts. FIG. 8 is a schematic diagram that represents an estimation algorithm for the detection and estimation of spontaneous breathing efforts for adult, pediatric, and neonatal ventilator patients. Spontaneous breathing efforts can be derived from a number of sensors and signals 94 available for a ventilator patient that include but are not limited to—patient flow sensor, respiratory effort belts, respiratory effort balloons (like Graseby sensor) for neonatal patients, photoplethysmogram, electro-responsive sensor films, accelerometers attached to body at appropriate body-sites. The data and/or signals from sensors 94 are processed in processor 96 along with HFV user setting 98. A determination of spontaneous breathing effort results in a signal to HFV control 100.

Figure 9:
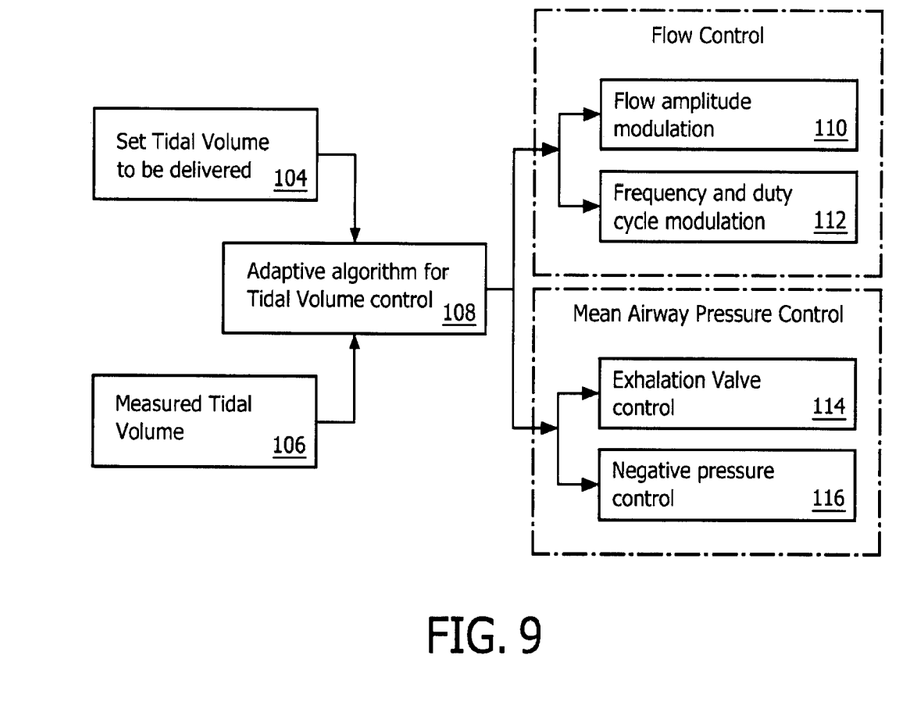
FIG. 9 is a schematic representation of an algorithm for tidal volume control.

In another embodiment of the invention, an algorithm adaptively sets the high frequency ventilation (e.g., frequency, flow levels, or mean airway pressure) to deliver a set sub-physiologic or physiologic tidal volume, i.e., flow over time. Additionally, another embodiment of the invention can include an algorithm to adaptively set the high frequency ventilation (e.g., frequency, flow levels, or mean airway pressure) to deliver a measured tidal volume. The implementation will include adaptively changing the high frequency ventilation by changing the flow amplitude modulation and/or frequency modulation along with the manipulation of the mean airway pressure with control of exhalation valve and/or applying negative pressure. The algorithm is schematically represented in FIG. 9, where data regarding the set tidal volume 104 and measured tidal volume 106 are inputted to a processor 108. Signals from processor 108 result in adjustments to flow amplitude 110, frequency modulation 112, exhalation valve control 114, and/or negative pressure control 116.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. A method of providing high frequency positive pressure ventilation (HFPPV) to a patient, comprising acts of:
    delivering a flow of breathing gas to the patient, the flow of breathing gas having a first positive pressure level and a second positive pressure level, the first and second positive pressure levels alternating with one another in a plurality of cycles in the flow of breathing gas to have a frequency and an amplitude, the flow of breathing gas to the patient generating a mean airway pressure and having a flow amplitude;
    performing by a controller a determination of spontaneous breathing efforts by the patient, wherein the spontaneous breathing efforts comprise one of a spontaneous breathing, an attempt at spontaneous breathing and non-spontaneous breathing;
    performing by the controller a simultaneous control of: an adjustment of the mean airway pressure, a modulation of the frequency and a duty cycle of the flow of breathing gas, and a modulation of the flow amplitude of the flow of breathing gas, to implement an HFPPV mode with an extended range for the frequency, the duty cycle, a flow level, and the mean airway pressure of positive pressure ventilation including 2 Hz and 25 Hz based on the simultaneous control; and
    providing by the controller physiologic volumes interspersed with high frequency sub-physiologic volumes by intermittently modulating the mean airway pressure, wherein the mean airway pressure is modulated by intermittently applying a negative pressure, wherein the simultaneous control and the implementing of the HFPPV mode is in response to the determination, and wherein the HFPPV mode is implemented by delivering the modulated flow of breathing gas via a pressure generating system through a patient circuit, in accordance with the adjusted mean airway pressure, and the modulated frequency and duty cycle.

2. The method of claim 1, wherein the mean airway pressure of the patient is further controlled by adjusting an exhalation resistance.

3. The method of claim 2, wherein the adjusting an exhalation resistance comprises adjusting an active exhalation valve.

4. The method of claim 3, wherein the active exhalation valve, the frequency and an inspiratory time of the flow of breathing gas, and the flow level of the breathing gas are controlled proportionally to a spontaneous breathing pattern.

5. The method of claim 3, wherein the active exhalation valve, the frequency and the duty cycle of the flow of breathing gas, and the flow level of the breathing gas are controlled in a bi-level manner for inhalation and exhalation phases of a spontaneous breathing pattern of the spontaneous breathing efforts.

6. The method of claim 3, wherein the active exhalation valve, the frequency and the duty cycle of the flow of breathing gas, and the flow level of the breathing gas are controlled in a manner as determined by user settings for high frequency ventilation (HFV) and a user intervention.

7. A high frequency positive pressure ventilation (HFPPV) support system, comprising:
a pressure generating system;
a negative pressure generating system;
a patient circuit operatively coupled to the pressure generating system and the negative pressure generating system and adapted to be coupled to a patient; and
a controller operatively coupled to the pressure generating system and the negative pressure generating system, the controller being configured to:
control the pressure generating system to deliver a flow of breathing gas to the patient through the patient circuit, the flow of breathing gas having a first positive pressure level and a second positive pressure level, the first and second positive pressure levels alternating with one another in a plurality of cycles in the flow of breathing gas to have a frequency and an amplitude, the flow of breathing gas having a mean airway pressure and a flow amplitude;
perform a determination of spontaneous breathing efforts by the patient;
wherein the spontaneous breathing efforts comprise one of a spontaneous breathing, an attempt at spontaneous breathing and non-spontaneous breathing,
the controller being further configured to:
perform a simultaneous control of: an adjustment of the mean airway pressure, a modulation of the frequency and a duty cycle of the flow of breathing gas, and a modulation of the flow amplitude of the flow of breathing gas;
implement an HFPPV mode with an extended range for the frequency, the duty cycle, a flow level of breathing gas, and the mean airway pressure of a positive pressure ventilation including 2 Hz and 25 Hz based on the simultaneous control; and provide physiologic volumes interspersed with high frequency sub-physiologic volumes by intermittently modulating the mean airway pressure, wherein the mean airway pressure is modulated by intermittently varying a negative pressure generated by the negative pressure generating system, wherein the simultaneous control and the implementing of the HFPPV mode is in response to the determination.

8. The pressure support system of claim 7, wherein the mean airway pressure is further controlled by adjusting an exhalation resistance.

9. The pressure support system of claim 7, wherein the adjusting an exhalation resistance comprises adjusting an active exhalation valve.

10. The pressure support system of claim 9, wherein the active exhalation valve, the frequency and the duty cycle of the flow of breathing gas, and the flow level of the breathing gas are controlled proportionally to a spontaneous breathing pattern of the spontaneous breathing efforts.

11. The pressure support system of claim 9, wherein the active exhalation valve, the frequency and the duty cycle of the flow of breathing gas, and the flow level of the breathing gas are controlled in a bi-level manner for an inhalation and an exhalation phases of a spontaneous breathing pattern of the spontaneous breathing efforts.

12. The pressure support system of claim 9, wherein the active exhalation valve, the frequency and the duty cycle of the flow of breathing gas, and the flow level of the breathing gas are controlled in a bi-level manner as determined by user settings for high frequency ventilation and a user intervention.

13. The pressure support system of claim 7, wherein the controller is further configured to provide physiologic volumes interspersed with high frequency sub-physiologic volumes by intermittently modulating the mean airway pressure, wherein the mean airway pressure is modulated by intermittently varying the flow amplitude of the flow of breathing gas.

14. The pressure support system of claim 7, wherein the controller is further configured to provide providing physiologic volumes interspersed with high frequency sub-physiologic volumes by intermittently modulating the mean airway pressure, wherein the mean airway pressure is modulated by intermittently varying the frequency.

15. The pressure support system of claim 7, wherein the controller is further configured to provide physiologic volumes interspersed with high frequency sub-physiologic volumes by intermittently modulating the mean airway pressure, wherein the mean airway pressure is modulated by intermittently varying the duty cycle.

16. The pressure support system of claim 7, wherein the mean airway pressure is modulated by intermittently varying one of the exhalation resistance, the amplitude, the frequency, the duty cycle, and combinations thereof.

17. The pressure support system of claim 7, wherein the controller is further configured to provide physiologic volumes interspersed with high frequency sub-physiologic volumes by intermittently modulating the mean airway pressure, wherein modulating the mean airway pressure is configured to achieve physiologic volumes to provide for the spontaneous breathing.

18. The pressure support system of claim 7, wherein the controller is further configured to provide physiologic volumes interspersed with high frequency sub-physiologic volumes by intermittently modulating the mean airway pressure, wherein modulating the mean airway pressure is configured to achieve one selected from the group consisting of physiologic volumes to provide for the spontaneous breathing with a pressure support and physiologic volumes in an absence of the spontaneous breathing.

19. A high frequency support system, comprising:
   a pressure generating system;
   a negative pressure generating system;
   a patient circuit operatively coupled to the pressure generating system and the negative pressure generating system and configured for being coupled to a patient; and
   a controller operatively coupled to the pressure generating system, the controller being configured to:
      control the pressure generating system to deliver a flow of breathing gas to the patient through the patient circuit, the flow of breathing gas having a first positive pressure level and a second positive pressure level, the first and second positive pressure levels alternating with one another in a plurality of cycles in the flow of breathing gas to have a frequency and an amplitude, the flow of breathing gas having a mean airway pressure and a flow amplitude;
      perform a determination of spontaneous breathing efforts by the patient;
   wherein the spontaneous breathing efforts comprise one of a spontaneous breathing, an attempt at spontaneous breathing and non-spontaneous breathing,
   the controller being further configured to:
      simultaneously control an adjustment of the mean airway pressure, a modulation of the frequency and a duty cycle of the flow of breathing gas, and a modulation of the flow amplitude of the flow of breathing gas;
      implement an HFPPV mode with an extended range for the frequency, the duty cycle, a flow level of breathing gas, and the mean airway pressure of a positive pressure ventilation including 2 Hz and 25 Hz based on the simultaneous control; and
      provide physiologic volumes interspersed with high frequency sub-physiologic volumes by intermittently modulating the mean airway pressure,
   wherein the mean airway pressure is modulated by intermittently varying a negative pressure with the negative pressure generating system, and
   wherein the simultaneous control and the implementing of the HFPPV mode is in response to the determination.

* * * * *